US00PP21489P2

(12) United States Plant Patent
Dümmen

(10) Patent No.: US PP21,489 P2
(45) Date of Patent: Nov. 16, 2010

(54) ***PELARGONIUM* PLANT NAMED 'DUESAWISPLA'**

(50) Latin Name: *Pelargonium zonale*
Varietal Denomination: Duesawispla

(75) Inventor: Tobias Dümmen, Rheinberg (DE)

(73) Assignee: Capital Green Investments Ltd., Grand Caymans (KY)

( * ) Notice: Subject to any disclaimer, the term of this patent is extended or adjusted under 35 U.S.C. 154(b) by 0 days.

(21) Appl. No.: 12/586,399

(22) Filed: Sep. 21, 2009

(51) Int. Cl.
*A01H 5/00* (2006.01)

(52) U.S. Cl. ..... Plt./329

(58) Field of Classification Search ..... Plt./325, Plt./329

See application file for complete search history.

*Primary Examiner*—Annette H Para
(74) *Attorney, Agent, or Firm*—C. A. Whealy

(57) ABSTRACT

A new and distinct cultivar of Zonal *Geranium* plant named 'Duesawispla', characterized by its upright to outwardly spreading plant habit; vigorous growth habit; freely basal branching habit; dark green-colored leaves with zonation pattern; freely flowering habit; semi-double very light purple-colored flowers; and good garden performance.

1 Drawing Sheet

Botanical designation: *Pelargonium zonale.*
Cultivar denomination: 'Duesawispla'.

BACKGROUND OF THE INVENTION

The present invention relates to a new and distinct cultivar of Zonal *Geranium* plant, botanically known as *Pelargonium zonale*, and hereinafter referred to by the name 'Duesawispla'.

The new Zonal *Geranium* plant is a product of a planned breeding program conducted by the Inventor in Rheinberg, Germany. The objective of the breeding program is to create new vigorous Zonal *Geranium* plants with dark green-colored leaves and attractive flowers.

The new Zonal *Geranium* plant originated from a cross-pollination made by the Inventor in July, 2005 in Rheinberg, Germany of a proprietary selection of *Pelargonium zonale* identified as code number Z02-0009-12, not patented, as the female, or seed, parent with a proprietary selection of *Pelargonium zonale* identified as code number Z02-0029-002, not patented, as the male, or pollen, parent. The new Zonal *Geranium* plant was discovered and selected by the Inventor as a single flowering plant from within the progeny of the stated cross-pollination in a controlled greenhouse environment in Rheinberg, Germany in May, 2008.

Asexual reproduction of the new Zonal *Geranium* plant by vegetative terminal cuttings in a controlled greenhouse environment in Rheinberg, Germany since May, 2008, has shown that the unique features of this new Zonal *Geranium* plant are stable and reproduced true to type in successive generations.

SUMMARY OF THE INVENTION

Plants of the new Zonal *Geranium* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Duesawispla'.

These characteristics in combination distinguish 'Duesawispla' as a new and distinct cultivar of Zonal *Geranium*:

1. Upright to outwardly spreading plant habit.
2. Vigorous growth habit.
3. Freely basal branching habit.
4. Dark green-colored leaves with zonation pattern.
5. Freely flowering habit.
6. Semi-double very light purple-colored flowers.
7. Good garden performance.

Plants of the new Zonal *Geranium* differ primarily from plants of the parent selections in flower color.

Plants of the new Zonal *Geranium* can be compared to plants of *Pelargonium zonale* 'Astra White', not patented. In side-by-side comparisons conducted in Rheinberg, Germany, plants of the new Zonal *Geranium* differed from plants of 'Astra White' in the following characteristics:

1. Plants of the new Zonal *Geranium* were more compact than plants of 'Astra White'.
2. Plants of the new Zonal *Geranium* and 'Astra White' differed slightly in flower color.

BRIEF DESCRIPTION OF THE PHOTOGRAPH

The accompanying colored photograph illustrates the overall appearance of the new Zonal *Geranium* plant, showing the colors as true as it is reasonably possible to obtain in colored reproductions of this type. Colors in the photograph may differ slightly from the color values cited in the detailed botanical description which accurately describe the colors of the new Zonal *Geranium* plant. The photograph comprises a side perspective view of a typical flowering plant of 'Duesawispla' grown in a container.

DETAILED BOTANICAL DESCRIPTION

The aforementioned photograph and following observations and measurements describe plants grown in 10.5-cm containers in Rheinberg, Germany in a glass-covered greenhouse during the summer and under conditions which closely approximate commercial production. During the production of the plants, day and night temperatures averaged 18° C. and light levels averaged 4,500 lux. Plants were pinched one time three weeks after planting. Plants had been growing for 13 weeks when the photograph and the description were taken. In the detailed description, color references are made to The Royal Horticultural Society Colour Chart, 1995 Edition, except where general terms of ordinary dictionary significance are used.

Botanical classification: *Pelargonium zonale* 'Duesawispla'.

Parentage:

*Female, or seed, parent.*—Proprietary selection of *Pelargonium zonale* identified as code number Z02-0009-12, not patented.

*Male or pollen parent.*—Proprietary selection of *Pelargonium zonale* identified as code number Z02-0029-002, not patented.

Propagation:

*Type.*—By vegetative terminal cuttings.

*Time to initiate roots, summer.*—About five days at temperatures of 20° C.

*Time to initiate roots, winter.*—About seven days at temperatures of 20° C.

*Time to produce a rooted young plant, summer.*—About three weeks at temperatures of 20° C.

*Time to produce a rooted young plant, winter.*—About four weeks at temperatures of 20° C.

*Root description.*—Fine, fibrous; white in color.

*Rooting habit.*—Freely branching.

Plant description:

*General appearance.*—Upright to outwardly spreading plant habit; uniformly rounded; densely foliated.

*Growth and branching habit.*—Vigorous growth habit; freely basal branching habit with about three basal branches developing per plant; pinching enhances lateral branch development.

*Plant height to top of flower umbels.*—About 21 cm.

*Plant height to top of foliar plane.*—About 17 cm.

*Plant width.*—About 23 cm.

*Lateral branches.*—Length: About 6 cm. Diameter: About 1 cm. Internode length: About 1.25 cm. Texture: Pubescent. Strength: Moderately strong. Color: Close to 144A.

Foliage description:

*Arrangement.*—Alternate; simple.

*Length.*—About 6.2 cm.

*Width.*—About 7.8 cm.

*Shape.*—Reniform.

*Apex.*—Acute.

*Base.*—Cordate.

*Margin.*—Crenate.

*Venation pattern.*—Palmate.

*Texture, upper surface.*—Pubescent.

*Texture, lower surface.*—Smooth, glabrous.

*Color.*—Developing leaves, upper and lower surfaces: Close to 137A. Fully expanded leaves, upper surface: Close to 139A; venation, close to 144A. Fully expanded leaves, lower surface: Close to 137A; venation, close to 144A. Zonation pattern: Distinct. Distance from margin: About 5 mm. Width: About 1.4 cm. Color: Close to 139A.

*Petiole.*—Length: About 5.8 cm. Diameter: About 2.8 mm. Texture, upper and lower surfaces: Smooth, glabrous. Color, upper and lower surfaces: Close to 143A.

Flower description:

*Flower arrangement.*—Semi-double rotate flowers arranged in rounded hemispherical umbels arising from apical leaf axils; umbels displayed above the foliage on moderately strong peduncles; flowers face upright to outward.

*Fragrance.*—Not detected.

*Quantity of flowers.*—Freely flowering habit; about 20 flowers and flower buds per umbel.

*Flowering season.*—Year-round under greenhouse conditions; in outdoor nurseries and gardens in Germany flowering is continuous from spring throughout the summer; plants begin flowering about eight weeks after planting.

*Flower longevity.*—Individual flowers last about five to seven days on the plant; flowers persistent.

*Umbel height.*—About 4.5 cm.

*Umbel diameter.*—About 8 cm.

*Flower diameter.*—About 4.5 cm.

*Flower depth (height).*—About 2.4 cm.

*Flower buds.*—Length: About 1.3 cm. Diameter: About 6.6 mm. Shape: Ovoid. Color: Close to 150D.

*Petals.*—Quantity per flower: About five. Length: About 2.7 cm. Width: About 2.3 cm. Shape: Obovate. Apex: Rounded. Base: Attenuate. Margin: Sinuate. Texture, upper and lower surfaces: Smooth, glabrous. Color: When opening, upper surface: Close to 69C to 69D. When opening, lower surface: Close to 155B. Fully opened, upper surface: Close to 76D; color becoming closer to 73D with development. Fully opened, lower surface: Close to 76D; color becoming closer to 73C with development.

*Petaloids.*—Quantity per flower: About two to three. Length: About 1.8 cm. Width: About 1.2 cm. Shape: Obovate. Apex: Rounded. Base: Attenuate. Margin: Sinuate. Texture, upper and lower surfaces: Smooth, glabrous. Color: When opening, upper surface: Close to 69B. When opening, lower surface: Close to 155A. Fully opened, upper surface: Close to 69D. Fully opened, lower surface: Close to 76D.

*Sepals.*—Quantity per flower: Five, arranged in a single whorl. Length: About 1.1 cm. Width: About 2.7 mm. Shape: Ensiform. Apex: Apiculate. Base: Acute. Margin: Entire. Texture, upper and lower surfaces: Smooth, glabrous. Color, upper and lower surfaces: Close to 144A.

*Peduncle (umbel stem).*—Length: About 10.2 cm. Diameter: About 3.5 mm. Strength: Moderately strong. Texture: Smooth, glabrous. Color: Close to 165A.

*Pedicel (individual flower stem).*—Length: About 2.3 cm. Diameter: About 1.5 mm. Strength: Moderately strong. Texture: Smooth, glabrous. Color: Close to 165A.

*Reproductive organs.*—Androecium: Stamen quantity per flower: About six. Filament length: About 7 mm. Filament color: Close to 155A. Anther length: About 2 mm. Anther shape: Oval. Anther color: Close to 66C. Pollen amount: Moderate. Pollen color: Close to 28A. Gynoecium: Pistil quantity per flower: One. Pistil length: About 4 mm. Stigma shape: Parted. Stigma color: Close to 50D. Style length: About 2 mm. Style color: Close to 151B. Ovary color: Close to 59A.

*Seed/fruit.*—Seed and fruit development have not been observed.

Disease/pest resistance: Plants of the new Zonal *Geranium* have not been observed to be resistant to pathogens and pests common to Zonal *Geraniums*.

Garden performance: Plants of the new Zonal *Geranium* have been observed to tolerate rain, wind, and temperatures ranging from about 5° C. to about 40° C. and have demonstrated good garden performance.

It is claimed:

1. A new and distinct Zonal *Geranium* plant named 'Duesawispla' as illustrated and described.

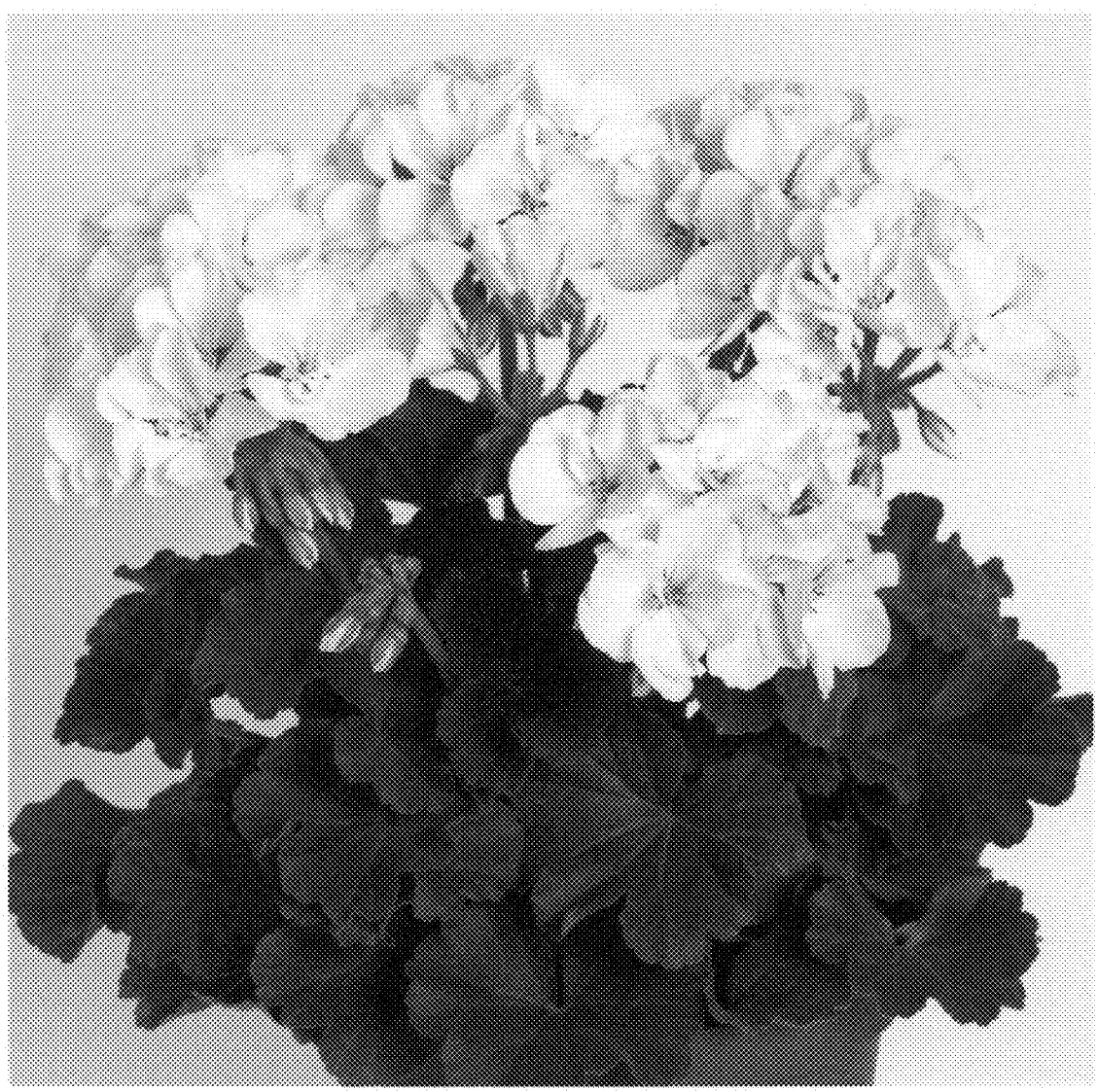

* * * * *